(12) United States Patent
Takeda

(10) Patent No.: US 11,744,525 B2
(45) Date of Patent: Sep. 5, 2023

(54) ULTRASOUND DIAGNOSIS APPARATUS WITH ENHANCED IMAGE RESOLUTION

(71) Applicant: Konica Minolta, Inc., Tokyo (JP)

(72) Inventor: Yoshihiro Takeda, Hachioji (JP)

(73) Assignee: KONICA MINOLTA, INC., Tokyo (JP)

( * ) Notice: Subject to any disclaimer, the term of this patent is extended or adjusted under 35 U.S.C. 154(b) by 987 days.

(21) Appl. No.: 16/377,408

(22) Filed: Apr. 8, 2019

(65) Prior Publication Data

US 2019/0350533 A1 Nov. 21, 2019

(30) Foreign Application Priority Data

May 15, 2018 (JP) ................................. 2018-094034

(51) Int. Cl.
*A61B 8/08* (2006.01)
*A61B 8/00* (2006.01)
(Continued)

(52) U.S. Cl.
CPC .......... *A61B 5/7267* (2013.01); *A61B 8/5207* (2013.01); *A61B 8/54* (2013.01);
(Continued)

(58) Field of Classification Search
CPC ....... A61B 5/7267; A61B 8/5207; A61B 8/54; G06T 2207/10132; G06T 2207/20081;
(Continued)

(56) References Cited

U.S. PATENT DOCUMENTS

2013/0019685 A1* 1/2013 Sakaguchi ........... A61B 8/5207
73/602
2015/0018685 A1* 1/2015 Barker ................. A61B 8/4461
600/459
(Continued)

FOREIGN PATENT DOCUMENTS

JP 2008-100068 A 5/2008
JP 2010-022817 A 2/2010

OTHER PUBLICATIONS

"Image Super-Resolution Using Deep Convolutional Networks", Chao Dong, et al., arXiv: 1501.00092v3 [cs.CV] Jul. 31, 2015; pp. 1-14.

(Continued)

*Primary Examiner* — Amelie R Davis
(74) *Attorney, Agent, or Firm* — LUCAS & MERCANTI, LLP

(57) ABSTRACT

An ultrasound diagnosis apparatus includes: a transmission/reception part that sequentially supplies a drive signal to each of a plurality of ultrasound transducers, and receives and processes a reception signal output from each of the plurality of ultrasound transducers; and a hardware processor that: converts sampling data of each of positions into pixel values, and generates a first ultrasound image; upscales the first ultrasound image in accordance with a predetermined sample number increase magnification, and thereafter applies resolution enhancement processing on the first ultrasound image and thereby generates a second ultrasound image; converts the second ultrasound image into a display image; and controls transmission/reception conditions of the transmission/reception part so that an image size of the second ultrasound image becomes close to an image size of the display image, on the basis of the image size of the (Continued)

display image and the sample number increase magnification.

12 Claims, 14 Drawing Sheets

(51) Int. Cl.
    *A61B 5/00*      (2006.01)
    *G06T 3/40*      (2006.01)
    *G06T 7/40*      (2017.01)

(52) U.S. Cl.
    CPC .......... *G06T 3/4007* (2013.01); *G06T 3/4053* (2013.01); *G06T 7/40* (2013.01); *G06T 2207/10132* (2013.01); *G06T 2207/20081* (2013.01); *G06T 2207/20084* (2013.01); *G06T 2207/30004* (2013.01)

(58) Field of Classification Search
    CPC . G06T 2207/20084; G06T 2207/30004; G06T 3/4007; G06T 3/4053; G06T 7/40
    See application file for complete search history.

(56) References Cited

U.S. PATENT DOCUMENTS

2015/0065867 A1* 3/2015 Cho ..................... A61B 8/464
                                                600/424
2016/0361044 A1* 12/2016 Hibi ..................... A61B 8/54

OTHER PUBLICATIONS

"RAISR: Rapid and Accurate Image Super Resolution", Yaniv Romano, et al., arXiv:1606.01299v3 [cs.CV] Oct. 4, 2016; pp. 1-31.

* cited by examiner

FIRST ULTRASOUND IMAGE D2a
AFTER ENLARGEMENT

| R1  | R2  | R3  | R4  | R5  | R6  |
|-----|-----|-----|-----|-----|-----|
| R7  | R8  | R9  | R10 | R11 | R12 |
| R13 | R14 | R15 | R16 | R17 | R18 |
| R19 | R20 | R21 | R22 | R23 | R24 |
| R25 | R26 | R27 | R28 | R29 | R30 |
| R31 | R32 | R33 | R34 | R35 | R36 |

ULTRASOUND DIAGNOSIS APPARATUS WITH ENHANCED IMAGE RESOLUTION

The entire disclosure of Japanese patent Application No. 2018-094034, filed on May 15, 2018, is incorporated herein by reference in its entirety.

BACKGROUND

Technological Field

The present disclosure relates to an ultrasound diagnosis apparatus.

Description of the Related art

There is a known ultrasound diagnosis apparatus that uses a plurality of ultrasound transducers to image a tissue portion within a subject.

This type of ultrasound diagnosis apparatus uses ultrasounds transmitted from a plurality of ultrasound transducers to scan within the subject and receives an echo reflected within the subject. On the basis of the strength of the ultrasound echo received, the ultrasound diagnosis apparatus obtains image information (hereinafter referred to as an ultrasound image) regarding the tissue portion (for example, internal organs or diseased tissue) within the subject.

Meanwhile, in order to achieve detailed observation of both the structure and the movement of the tissue portion, this type of ultrasound diagnosis apparatus needs to achieve both enhanced resolution of the ultrasound image displayed by a display part and a higher frame rate of generating the ultrasound image (the number of frames of the ultrasound image generated per unit time, the same will apply in the following).

FIG. 1 is a view illustrating an example of a scanning mode in generating an ultrasound image of one frame.

As illustrated in FIG. 1, this type of ultrasound diagnosis apparatus includes a plurality of ultrasound transducers T1 arranged in an azimuth direction, within an ultrasound probe T. Subsequently, ultrasound transmission/reception is executed such that the plurality of ultrasound transducers T1 is sequentially driven in unit of a single piece or unit of group from one side to the other side in the azimuth direction so as to scan within the subject, thereby generates an ultrasound image of one frame.

To achieve higher resolution of the ultrasound image in this type of ultrasound diagnosis apparatus, it is typical to perform control to increase the number of scan lines for generating one frame of ultrasound image, that is, to increase the density of the scan line. This, however, leads to a problem that the higher the scan line density, the lower the frame rate becomes.

Meanwhile, in order to improve the frame rate at which an ultrasound image is generated in this type of ultrasound diagnosis apparatus, it is typical to perform control to decrease the number of scan lines, that is, to decrease the density of the scan lines for generating an ultrasound image of one frame. This, however, leads to a typical problem that the lower the scan line density, the lower the resolution of the ultrasound image to be generated.

In view of this background, there is a demand for a technique for achieving higher resolution of the ultrasound image displayed by the display part without deteriorating the frame rate.

For example, JP 2008-100068 A describes that an imaging scheme excellent in temporal resolution and an imaging scheme excellent in spatial resolution are selectively used according to an imaging target or the like. However, according to the known technology in JP 2008-100068 A, it is difficult to increase ultrasound image resolution without deteriorating the frame rate.

JP 2010-022817 A discloses a technique of combining an ultrasound image captured under a high density scan line condition at a first timing with an ultrasound image captured under a low density scan line condition at a second timing. However, the known technique according to JP 2010-022817 A needs to generate a plurality of ultrasound images necessary for combining an image, leading to small effects of effective frame rate improvement. Moreover, JP 2010-022817 A cannot increase the frame rate itself, it would be difficult to avoid inclusion of blurred regions in the combined ultrasound image due to movement of the tissue portion.

SUMMARY

The present disclosure has been made in view of the above problems and aims to provide an ultrasound diagnosis apparatus capable of increasing the resolution of an ultrasound image displayed by a display part without deteriorating the frame rate.

To achieve the abovementioned object, according to an aspect of the present invention, an ultrasound diagnosis apparatus reflecting one aspect of the present invention comprises: a transmission/reception part that sequentially supplies a drive signal to each of a plurality of ultrasound transducers provided in an ultrasound probe so as to scan within a subject, and receives and processes a reception signal output from each of the plurality of ultrasound transducers; and a hardware processor that: converts sampling data of each of positions within the subject generated on the basis of the reception signal into pixel values, and generates a first ultrasound image; upscales the first ultrasound image in accordance with a predetermined sample number increase magnification, and thereafter applies resolution enhancement processing on the first ultrasound image and thereby generates a second ultrasound image; converts the second ultrasound image into a display image to be displayed on a display part; and controls transmission/reception conditions of the transmission/reception part so that an image size of the second ultrasound image becomes close to an image size of the display image, on the basis of the image size of the display image and the sample number increase magnification.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention.

DETAILED DESCRIPTION OF EMBODIMENTS

Figure 1:
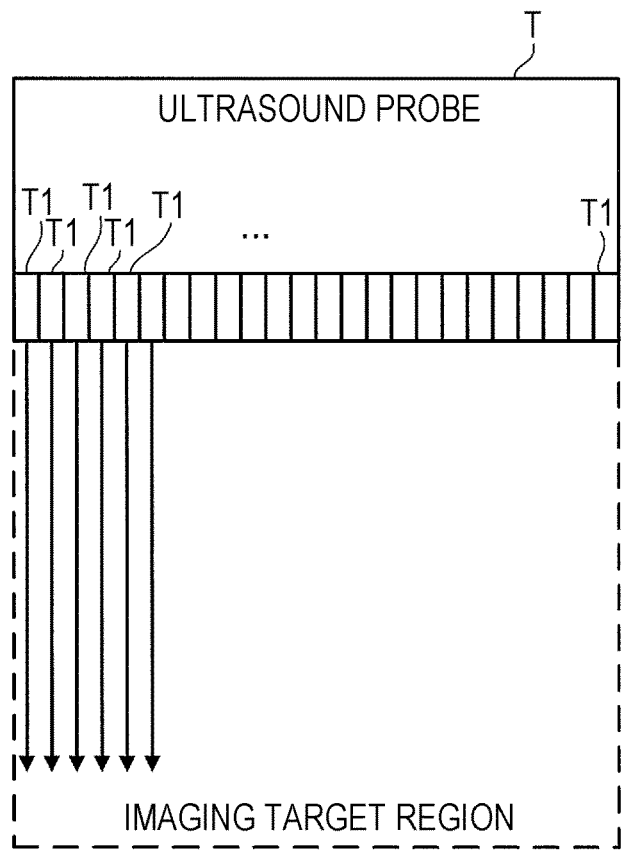
FIG. 1 is a view illustrating an example of a scanning mode in generating an ultrasound image of one frame.

Hereinafter, one or more embodiments of the present invention will be described with reference to the drawings. However, the scope of the invention is not limited to the disclosed embodiments. Note that in this specification and the drawings, the same reference numerals are given to constituent elements having substantially the same functional configuration, and redundant description will be omitted.

First Embodiment

[Entire Configuration of Ultrasound Diagnosis Apparatus 1]

Hereinafter, an example of an entire configuration of an ultrasound diagnosis apparatus 1 according to the present embodiment will be described with reference to FIGS. 2 to 4.

In the following, an example of control when the ultrasound diagnosis apparatus 1 according to the present embodiment generates a B-mode image will be described.

Figure 2:
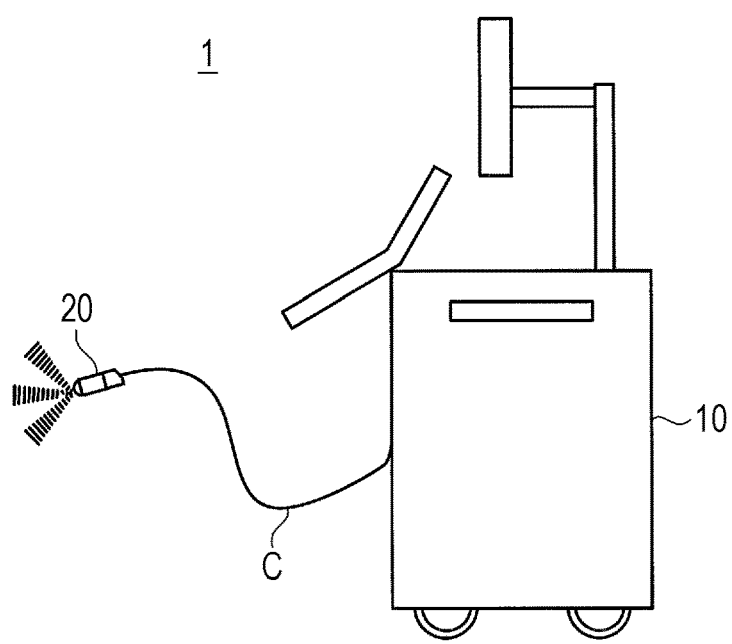
FIG. 2 is a view illustrating an appearance of an ultrasound diagnosis apparatus according to a first embodiment.

FIG. 2 is a view illustrating an appearance of the ultrasound diagnosis apparatus 1 according to the present embodiment. FIG. 3 is a block diagram illustrating an example of an overall configuration of the ultrasound diagnosis apparatus 1 according to the present embodiment. FIG. 4 is a view illustrating an example of an array structure of ultrasound transducers 21 of an ultrasound probe 20 according to the present embodiment.

The ultrasound diagnosis apparatus 1 according to the present embodiment has a configuration in which the ultrasound probe 20 is attached to a main body 10 of an ultrasound diagnosis apparatus 1 (hereinafter referred to as the "main body 10"). The main body 10 and the ultrasound probe 20 are electrically connected with each other via a cable C.

The main body 10 of the ultrasound diagnosis apparatus 1 includes a transmission/reception part 11, an image generation part 12, a resolution enhancement processing part 13, a digital scan converter 14, a display part 15, a transmission/reception control part 16, a mode setting part 17, and a learning processing part 18. Furthermore, the main body 10 includes model data Dm (hereinafter referred to as "CNN model Dm") of a convolutional neural network referred to by the resolution enhancement processing part 13.

Figure 3:
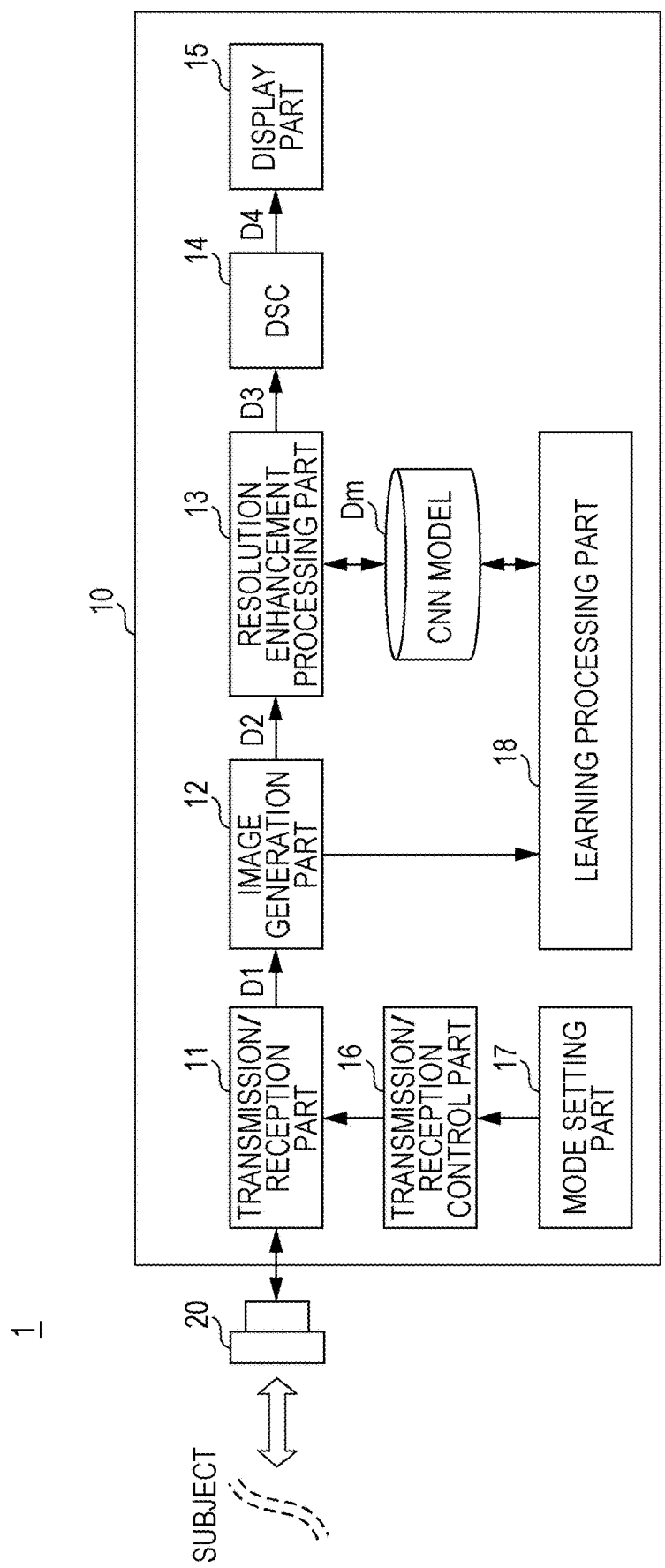
FIG. 3 is a block diagram illustrating an example of an overall configuration of the ultrasound diagnosis apparatus according to the first embodiment.

In FIG. 3, D1 represents data related to a reception signal generated by the transmission/reception part 11, D2 represents data related to an ultrasound image generated by the image generation part 12 (hereinafter referred to as a "first ultrasound image"), D3 represents data related to an ultrasound image generated by the resolution enhancement processing part 13 (hereinafter referred to as a "second ultrasound image"), and D4 represents data related to an image generated by the digital scan converter 14 to be displayed on the display part 15 (hereinafter referred to as a "display image").

In the following, the number of pixels included in an image of one frame will be referred to as "image size". The image size is typically defined on the basis of the number of pixels in a scanning direction and the number of pixels in a depth direction in the image of one frame.

The ultrasound probe 20 includes a plurality of ultrasound transducers 21 (for example, piezoelectric elements) configured to mutually convert ultrasounds and electric signals. The plurality of ultrasound transducers 21 individually converts voltage pulses generated by the transmission/reception part 11 into ultrasound beams and transmits the ultrasound beams into the subject. Together with this, the plurality of ultrasound transducers 21 receives ultrasound echoes as reflected ultrasound beams from the subject, converts the received ultrasound echoes into electric signals, and outputs the electric signals to the transmission/reception part 11.

Figure 4:
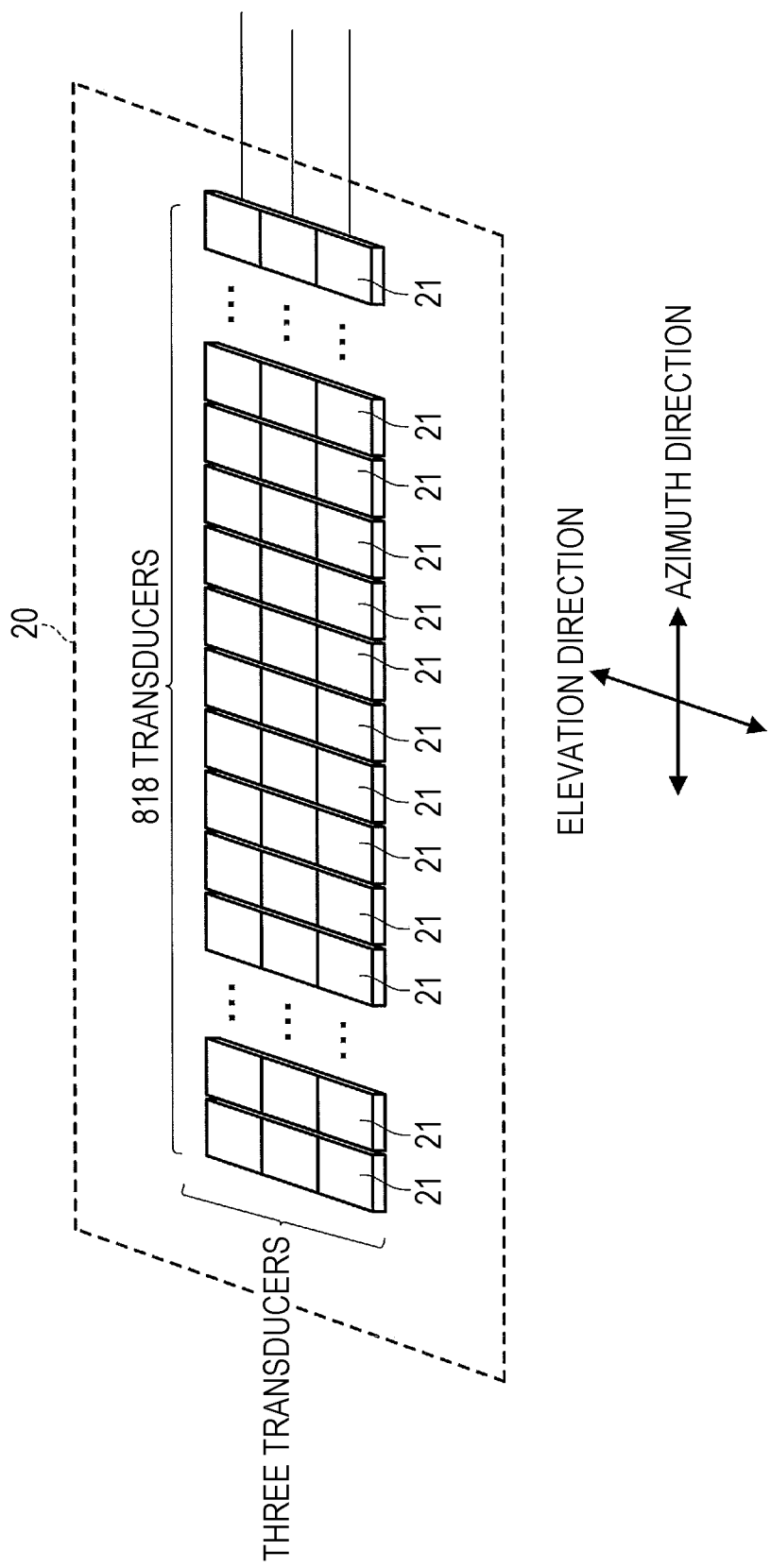
FIG. 4 is a view illustrating an example of an array structure of ultrasound transducers of the ultrasound probe according to the first embodiment.

The plurality of ultrasound transducers 21 is arrayed in matrix in an azimuth direction and an elevation direction (refer to FIG. 4). In the present embodiment, for example, 818 x 3 ultrasound transducers 21 are arranged in matrix in the azimuth direction and the elevation direction in a two-dimensional plane.

On-off switching of the driving states of the plurality of ultrasound transducers 21 is controlled sequentially in the azimuth direction individually or in units of blocks by the transmission/reception part 11. This allows for execution of transmission and reception of ultrasound in the ultrasound probe 20 so as to scan within the subject.

The transmission/reception part 11 is a transmission/reception circuit that causes the ultrasound transducer 21 of the ultrasound probe 20 to execute transmission and reception of ultrasound.

The transmission/reception part 11 includes: a transmission circuit that generates a voltage pulse (hereinafter referred to as a "drive signal") and transmits the voltage pulse to the ultrasound transducer 21; and a reception circuit that receives and processes an electric signal related to ultrasound echoes (hereinafter referred to as "reception signal") generated by the ultrasound transducer 21. Under the control of the transmission/reception control part 16, the transmission circuit and the reception circuit executes operation of controlling the ultrasound transducer 21 to transmit and receive ultrasound, respectively.

The transmission circuit of the transmission/reception part 11 includes, for example, a high-frequency pulse generator and a pulse setting part provided for each of the ultrasound transducers 21. The transmission circuit adjusts the voltage pulse generated by the high-frequency pulse generator to the voltage amplitude, pulse width and timing set in the pulse setting part, and transmits the adjusted voltage pulse to the ultrasound transducer 21.

Furthermore, the reception circuit of the transmission/reception part 11 includes a preamplifier, an AD converter, and a reception beam former. The preamplifier and the AD converter are provided for each of the ultrasound transducers 21, thereby amplifying a weak reception signal and converting the amplified reception signal (analog signal) into a digital signal. The reception beam former applies delay-and-sum on a reception signal (digital signal) of each of the ultrasound transducers 21 and combines reception signals D1 from the plurality of ultrasound transducers 21 into one, and then outputs the combined signals to the image generation part 12.

The transmission/reception control part 16 controls the transmission/reception part 11. The transmission/reception control part 16 controls the transmission/reception part 11 so as to drive the plurality of ultrasound transducers 21 sequentially in the scanning direction. For example, the transmission/reception control part 16 simultaneously drives groups of 50 ultrasound transducers 21 adjacent to each other among the 818 ultrasound transducers 21, shifts one or a plurality of the groups in the azimuth direction to scan within the subject. The transmission/reception control part 16 sequentially shifts the groups of 50 ultrasound transducers 21 as a driving target, from one side to the other side of the 818 ultrasound transducers 21, until completion of the scanning for one frame.

In order to continuously generate an ultrasound image, the transmission/reception control part 16 returns to an initial scanning position every time the scanning of one frame finishes, and executes the similar processing again.

The transmission/reception control part 16 determines transmission/reception conditions of the transmission/reception part 11 on the basis the type of the ultrasound probe 20 set by the mode setting part 17, the depth of the imaging target in the subject, or the operation mode (for example, B-mode, C-mode, or E-mode)

The "transmission/reception conditions" include scan line density at the time of scanning for generating an ultrasound image of one frame, sampling frequency for defining frequency of execution of sampling within one scan line, and depth. The transmission/reception control part 16 according to the present embodiment determines the "transmission/reception conditions" such that the image size of the second ultrasound image becomes the image size of the display image D4 or more and the frame rate at which the first ultrasound image D2 is generated is maximized (to be described below with reference to FIG. 8).

The mode setting part 17 sets a mode for operating the ultrasound diagnosis apparatus 1 on the basis of a user's operation input. The mode setting part 17 sets the type of the ultrasound probe 20, the depth of the imaging target within the subject, or the imaging mode (for example, the B-mode, the C-mode, or the E-mode) on the basis of user's operation input, for example. Furthermore, the mode setting part 17 may be configured to be able to set the image size and the image shape of the display image D4, for example, on the basis of the user's operation input.

The image generation part 12 obtains the reception signal D1 from the transmission/reception part 11 and sequentially accumulates the reception signals D1 at individual scanning positions output from the transmission/reception part 11 in a line memory, and then, generates two-dimensional data to be a frame unit. Note that the two-dimensional data includes signal strength information at individual positions in the cross section of the subject in the scanning direction and depth direction.

Subsequently, the image generation part 12 generates the first ultrasound image D2 on the basis of the two-dimensional data. For example, the image generation part 12 converts the sampling data (for example, the signal strength of the reception signal) at individual positions in the cross section in the scanning direction and the depth direction into a pixel value, and generates the first ultrasound image D2 for performing one-frame B-mode display. In addition, the image generation part 12 generates the first ultrasound image D2 every time the transmission/reception part 11 scans within the subject, for example.

The image generation part 12 may further perform logarithmic amplification, filtering (for example, low-pass transmission or smoothing, etc.), emphasis processing, dynamic range adjustment, or the like, on the reception signal input from the transmission/reception part 11.

The resolution enhancement processing part 13 obtains the first ultrasound image D2 from the image generation part 12, upscales the image size of the first ultrasound image D2. Together with this, the resolution enhancement processing part 13 uses the learned CNN model Dm and applies image analysis processing (for example, CNN forward propagation processing) on the upscaled first ultrasound image D2 (described below with reference to FIG. 7). In other words, the resolution enhancement processing part 13 generates the second ultrasound image D3 having resolution enhanced from the first ultrasound image D2.

The CNN model Dm includes, for example, structural data of the convolution neural network and data related to network parameters of the convolution neural network.

The digital scan converter 14 obtains the second ultrasound image D3 from the resolution enhancement processing part 13 and converts the image data of the second ultrasound image D3 into the display image data according to a television signal scanning scheme of the display part 15 (that is, the display image D4). In addition, the digital scan converter 14 may cut out a predetermined region from the second ultrasound image D3 in accordance with the display size in which the display part 15 displays the ultrasound image. The digital scan converter 14 may further perform aspect ratio adjustment processing or gradation processing for each of pixels onto the second ultrasound image D3.

Note that the image size and the image shape of the display image D4 are set by display layout set on the display part 15, the type of the ultrasound probe 20 to be used, the depth setting of the imaging target region, or the like.

An example of the display part 15 is a display such as a liquid crystal display (LCD). The display part 15 obtains image data related to the display image D4 from the digital scan converter 14, and displays the image data.

The learning processing part 18 performs learning processing on the CNN model Dm using the learning data (described below with reference to FIG. 9).

Figure 5:
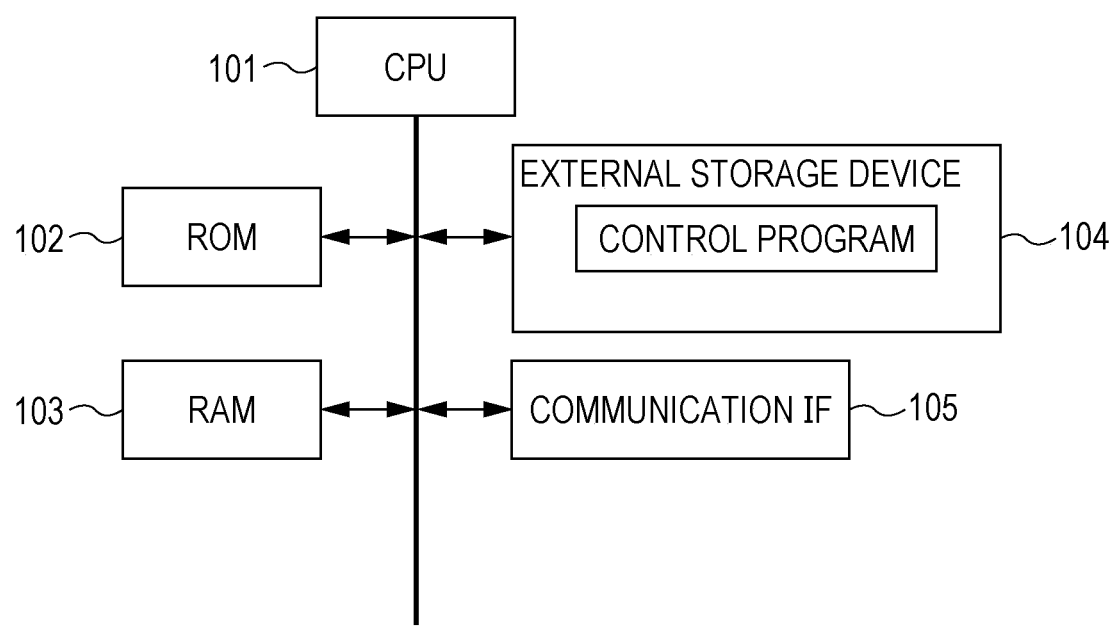
FIG. 5 illustrates an example of a hardware configuration of an image generation part, a resolution enhancement processing part, a digital scan converter, a transmission/reception control part, a mode setting part, and a learning processing part in the ultrasound diagnosis apparatus according to the first embodiment.

FIG. 5 illustrates an example of a hardware configuration of the image generation part 12, the resolution enhancement processing part 13, the digital scan converter 14, the transmission/reception control part 16, the mode setting part 17, and the learning processing part 18 in the ultrasound diagnosis apparatus 1 according to the present embodiment.

The image generation part 12, the resolution enhancement processing part 13, the digital scan converter 14, the transmission/reception control part 16, the mode setting part 17, and the learning processing part 18 each includes, for example, a central processing unit (CPU) 101, a read only memory (ROM) 102, a random access memory (RAM) 103, an external storage device 104, and a communication IF 105. Each of the functions described above is implemented by the CPU 101 when it refers to the control program and various types of data stored in the ROM 102 and the RAM 103. Implementation of some or all of the above-described functions is not limited to processing by software, and can also be achieved by dedicated hardware circuits or a combination of software and hardware. In addition, some or all of the above-described functions may be constituted by a digital arithmetic processing circuit such as a digital signal processor (DSP).

[Configuration of Resolution Enhancement Processing Part]

Hereinafter, a configuration of the resolution enhancement processing part 13 will be described in detail with reference to FIGS. 6 and 7.

Figure 6:
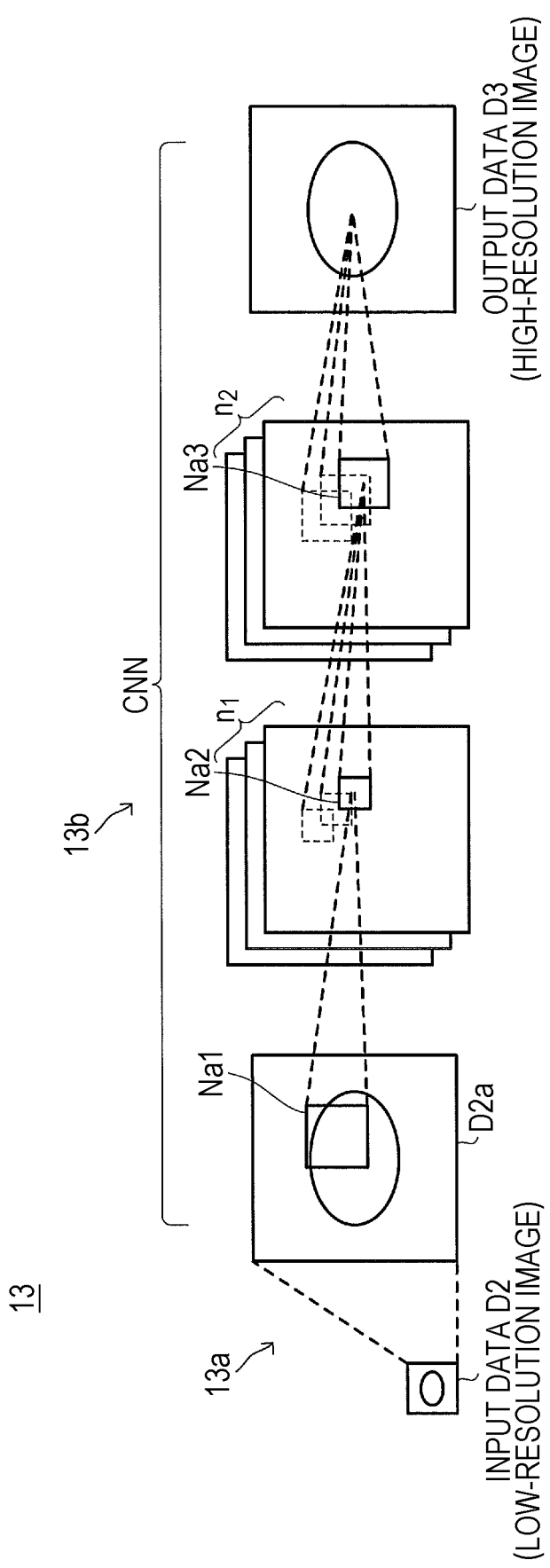
FIG. 6 is a diagram illustrating an example of a configuration of a resolution enhancement processing part according to the first embodiment.
Figure 7:
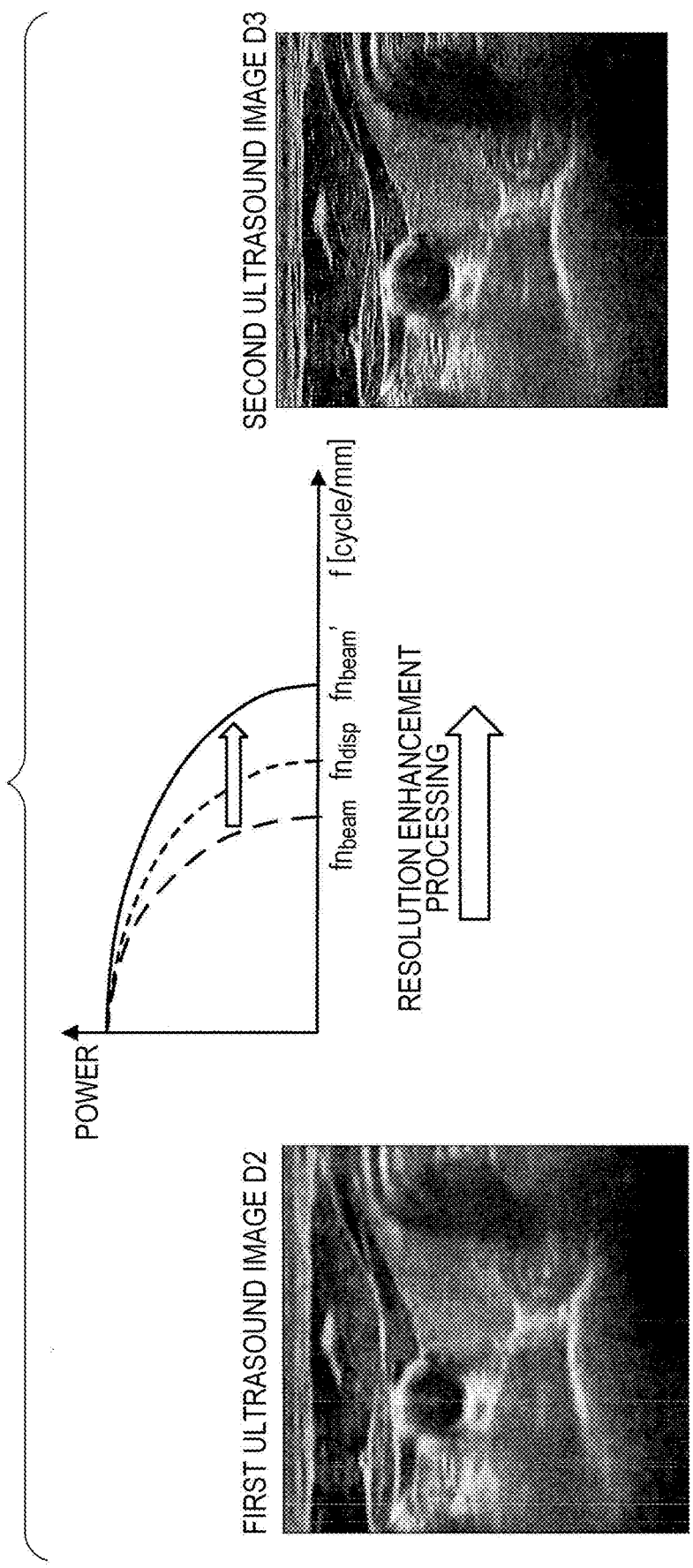
FIG. 7 is a view schematically illustrating processing of the resolution enhancement processing part according to the first embodiment.

FIG. 6 is a diagram illustrating an example of a configuration of the resolution enhancement processing part 13. FIG. 7 is a view schematically illustrating processing of the resolution enhancement processing part 13.

The resolution enhancement processing part 13 includes an image enlargement part 13a and a CNN processing part 13b, for example.

The image enlargement part 13a uses general-purpose image interpolation processing (for example, the Bicubic method or the Bilinear method) and interpolates between the pixels of the first ultrasound image D2, thereby upscaling an image size of the first ultrasound image D2 by a predetermined magnification (an image D2a in FIG. 6 represents an image after upscaling). The Bilinear method, for example, refers to the luminance values of pixels around a target pixel and calculates the luminance value of the target pixel such that the luminance values of the surrounding pixels change linearly.

The magnification at which the image enlargement part 13a enlarges the first ultrasound image D2 (hereinafter referred to as "sample number increase magnification") is preset for each of the scanning direction and the depth direction, for example, set to integers of 2×2 times, 3×3 times, 4×4 times, or the like. From the viewpoint of the learning efficiency of the CNN model Dm or the like, it is desirable that the sample number increase magnification be an integer of two or more.

The sample number increase magnification is more preferably set such that the greater the depth of the imaging target within the subject set by the mode setting part 17, the larger the sample number increase magnification. This setting is effective in radial scan such as trapezoidal scan performed by a convex probe, a sector probe, or a linear probe because the deeper the position, the wider the lateral distance of the reception beam.

Alternatively, the sample number increase magnification may be set on the basis of operator's input operation.

The CNN processing part 13b inputs the first ultrasound image D2a upscaled by the image enlargement part 13a to the learned CNN model Dm and thereby performs forward propagation processing on the CNN model Dm. This processing generates a second ultrasound image D3, a reconfigured image of the upscaled first ultrasound image D2a.

Note that applying the learned CNN model Dm is equivalent to estimating high frequency components in the upscaled first ultrasound image D2a. That is, the resolution enhancement processing part 13 enhances a Nyquist frequency $fn_{beam}$ defined from the sampling number at generation of the first ultrasound image D2 to a frequency $fn_{beam}'$ representable by the display image D4, that is, a Nyquist frequency $fn_{disp}$ (level of fineness represented by the display image D4 corresponding to resolution) or higher frequency (refer to FIG. 7).

The CNN model Dm includes a plurality of hierarchically connected filter layers Na1, Na2, and Na3 (here, illustrating simply three layers), for example.

The first filter layer Na1 scans an input image for each of predetermined sizes by raster scan. Then, the first filter layer Na1 applies feature amount extraction processing on the scanned data by using a convolution layer or the like and extracts the feature amount included in the input image The first filter layer Na1 extracts a relatively simple single feature amount such as a linear feature amount extending in the horizontal direction and a linear feature amount extending in the diagonal direction.

The second filter layer Na2 scans a group of images (hereinafter also referred to as "feature map") input from the filter layer Na1 of the preceding layer for each of predetermined sizes by raster scan, for example. The second filter layer Na2 similarly applies the feature amount extraction processing on the scanned data by using a convolution layer or the like and extracts feature amounts included in the input image. Note that the second filter layer Na2 performs integration in consideration of the positional relationship or the like of a plurality of feature amounts extracted by the first filter layer Na1, thereby extracting a composite feature amount with higher dimension.

In each of the filter layers Na1 and Na2, the convolution layer performs convolution operation on each of scanned pixel values of an image of a predetermined size by using a kernel that has set a weighting factor and a bias, and sequentially performs mapping. Subsequently, the convolution layer uses the kernel and performs convolution operation on each of the images input from the previous layer, and executes addition to the mapping position corresponding to the image region being a processing target, thereby generating one feature map.

Note that each of the filter layers Na1 and Na2 typically includes an activation layer and a pooling layer at the subsequent stage of the convolution layer. Then, the feature map generated by the convolution layer is output to the subsequent filter layer through the activation layer and the pooling layer.

The filter layers Na1 and Na2 generate a feature map to be output to the next hierarchy by a series of processing performed by the convolution layer, the activation layer, and the pooling layer. Next, the filter layers Na1 and Na2 execute the above processing using a plurality of kernels having different weight patterns and generate feature maps as many as the number of the plurality of kernels (ni and $n_2$ in FIG. 6 represent generated feature maps).

In this manner, feature extraction processing is repeated by a plurality of hierarchically connected filter layers Na1 and Na2, thereby extracting various feature amounts of the subject in the image with higher dimension.

The final filter layer Na3 functions as a deconvolution layer for generating an image having resolution enhanced from the input image from the feature map group generated by the filter layers Na1 and Na2. The filter layer Na3 includes, for example, a kernel of one convolution layer to which a weighting factor and a bias are set. Similarly to the filter layers Na1 and Na2, the filter layer Na3 scans the feature map input from the previous layer for each of predetermined sizes by raster scan. The filter layer Na3 further performs convolution operation on the scanned data in the feature map by using the kernel, and sequentially maps the data. The final filter layer Na3 performs convolution operation on each of the feature map groups input from the previous layer by using the kernel of the convolution layer and performs addition to the mapping position corresponding to the image region being a processing target, thereby generating the second ultrasound image D3.

The output of the final filter layer Na3 is typically set so that the second ultrasound image D3 has the same image size as the upscaled first ultrasound image D2a. In this manner, the second ultrasound image D3 having resolution enhanced from the upscaled first ultrasound image D2a is generated. For example, a pixel value expressed in the gradation range (for example, 0 to 255) similar to the first ultrasound image D2 is output onto each of pixels of the second ultrasound image D3.

The CNN model Dm undergoes learning processing by the learning processing part 18, thereby adjusting network parameters (for example, the weighting factor and the bias of the convolution layer), allowing the CNN model Dm to function as described above.

For image processing of enhancing resolution from the input image using the CNN model Dm, refer to Chao Dong, et al. "Image Super-Resolution Using Deep Convolutional Networks", arXiv: 1501.00092v3 [cs.CV], 31 Jul. 2015, for example.

The network parameter of the CNN model Dm according to the present embodiment has been optimized, for example, in the learning stage by using an original image of the first ultrasound image D2 and using a blurred image of the first ultrasound image D2 that is first reduced by Bilinear method and thereafter enlarged again with definition of the blurred image as an input image and the original image as the correct image (details will be described below).

Note that the CNN model Dm according to the present embodiment can be changed into various structures as long as it is a neural network that performs at least one convolution operation. The CNN model Dm may include, for example, a multilayer perceptron or a preprocessing layer. Moreover, the model may include a recurrent neural network.

[Configuration of Transmission/Reception Control Part]

The transmission/reception control part 16 controls the transmission/reception conditions of the transmission/reception part 11 so that the image size of the second ultrasound image D3 becomes close to the image size of the display image D4 on the basis of the image size of the display image D4 and the sample number increase magnification.

Here, the "transmission/reception conditions" include: the number of scan lines or the density of scan lines at generation of the first ultrasound image D2 (that is, the sampling number in the scanning direction in generating one frame of ultrasound image); and a sampling frequency at which sampling is performed in one scan line (that is, a sampling number in the depth direction).

The "transmission/reception conditions" define the image size of the first ultrasound image D2 and the frame rate at which the first ultrasound image D2 is to be generated. For example, in a case where a group of 50 ultrasound transducers 21 simultaneously driven out of the 818 ultrasound transducers 21 is shifted one by one in the azimuth direction, the sampling number (that is, the number of pixels) in the scanning direction would be 768. In another case where a group of 50 ultrasound transducers 21 simultaneously driven out of the 818 ultrasound transducers 21 is shifted three at a time in the azimuth direction, the sampling number (that is, the number of pixels) in the scanning direction would be 256.

Here, since the display image D4 is generated from the second ultrasound image D3, the resolution of the display image D4 depends on the image size of the second ultrasound image D3. That is, the larger the image size of the second ultrasound image D3, the higher the resolution of the display image D4 can be.

However, the image size that can be implemented in the display image D4 is restricted by the image size (the number of pixels) of the display part 15 itself. Therefore, even if the image size of the second ultrasound image D3 is made unnecessarily large, the resolution of the display image D4 is limited to the image size of the display image D4 by the Nyquist theorem, and additionally, due to an increase in the number of scan lines, it just leads to reduction in the frame rate at which the first ultrasound image D2 is generated.

Accordingly, the transmission/reception control part 16 in the present embodiment sets the ultrasound transmission/reception conditions on the basis of the settings of the mode setting part 17 and the sample number increase magnification set by the resolution enhancement processing part 13 (image enlargement part 13a). Specifically, the transmission/reception control part 16 determines the ultrasound transmission/reception conditions such that the image size of the second ultrasound image D3 becomes the image size of the display image D4 or more and the frame rate at which the first ultrasound image D2 is generated is maximized In other words, the transmission/reception control part 16 controls the transmission/reception conditions of the transmission/reception part 11 so that the image size of the second ultrasound image D3 becomes close to the image size of the display image D4. This makes it possible to achieve both resolution enhancement of the display image D4 and improvement of the frame rate at which the display image D4 is generated.

Figure 8:
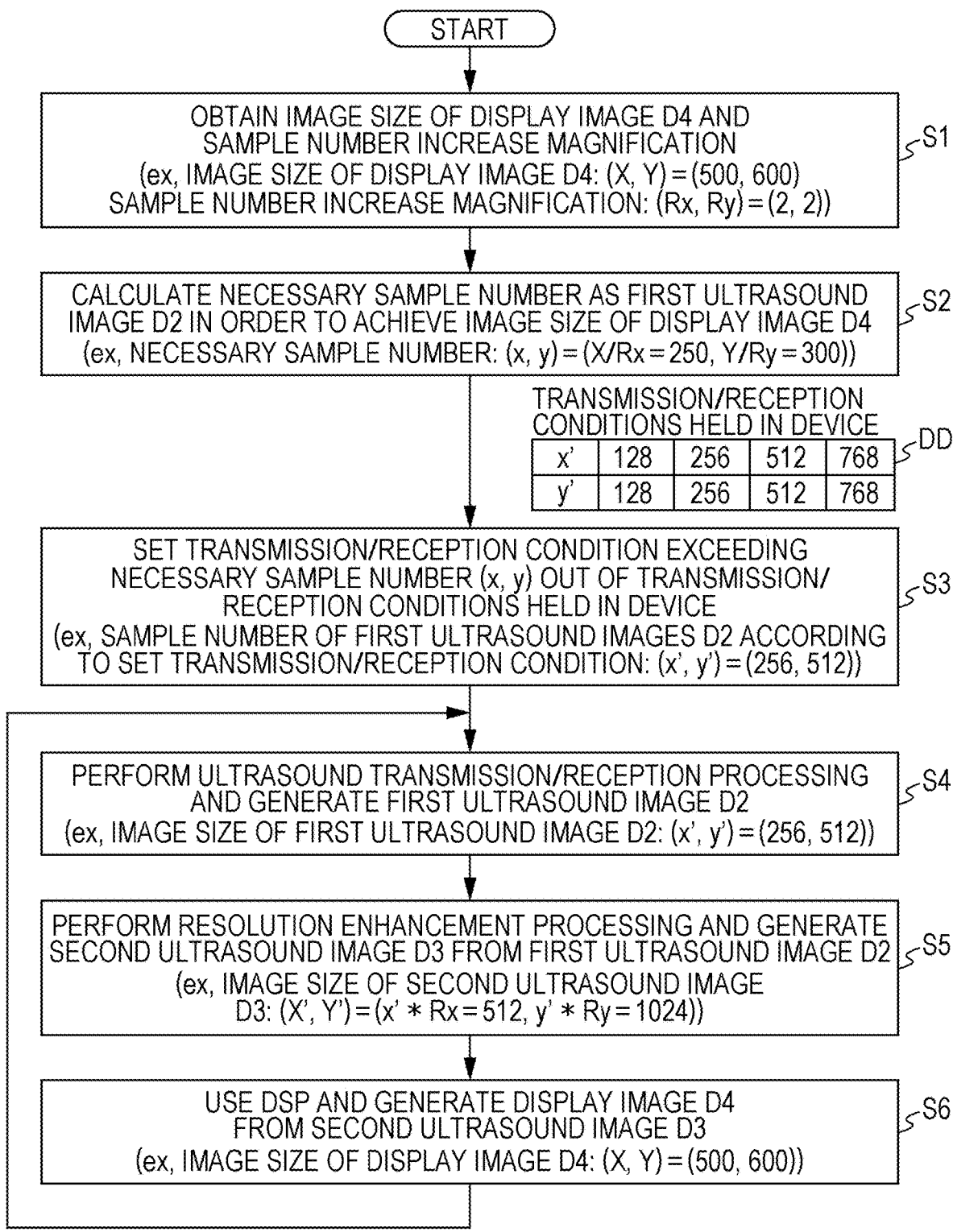
FIG. 8 is a flowchart illustrating an example of operation of the transmission/reception control part according to the first embodiment.

For example, the transmission/reception control part 16 selects one of the conditions enabling the image size of the second ultrasound image D3 to be close to the image size of the display image D4 from candidates of the transmission/reception conditions preliminarily stored in the ROM 102 or the like (for example, the data table DD related to the transmission/reception condition candidate illustrated in FIG. 8), and thereby determines ultrasound transmission/reception conditions that satisfy the above-described condition.

Note that "a state in which the image size of the second ultrasound image D3 becomes close to the image size of the display image D4" is ideally a state in which the image size of the second ultrasound image D3 is equal to the image size of the display image D4. Unfortunately, however, due to restrictions on executable transmission/reception conditions in practice, the transmission/reception control part 16 selects the transmission/reception condition such that the image size of the second ultrasound image D3 becomes closest to the image size of the display image D4 on the sides where the size is larger or smaller than the image size of the display image D4, out of the preliminarily stored candidates of transmission/reception conditions. At this time, more preferably, the transmission/reception control part 16 selects the candidate of the transmission/reception condition out of the preliminarily stored transmission/reception conditions enabling the image size of the second ultrasound image D3 to be the image size of the display image D4 or more and enabling the frame rate at which the first ultrasound image D2 is generated to be maximum. Alternatively, however, the transmission/reception control part 16 may make determination such that part of the transmission/reception conditions related to the scanning direction having a great influence on the frame rate satisfies the above condition.

Note that "transmission/reception conditions" are set to different conditions in accordance with the type of the ultrasound probe 20 set by the mode setting part 17, the setting of the depth of the imaging target in the subject, or the operation mode (for example, B-mode, C-mode, or E-mode)

FIG. 8 is a flowchart illustrating an example of operation of the transmission/reception control part 16. Note that FIG. 8 illustrates an example of set values set in each of flows to facilitate understanding.

In step S1, the transmission/reception control part 16 initially obtains the image size of the display image D4 defined from the settings of the mode setting part 17 and the sample number increase magnification in the resolution enhancement processing part 13. Note that it is assumed here, for example, that the image size of the display image D4 has been set to (X, Y)=(500, 600) (where X is the number of pixels in the scanning direction and Y is the number of pixels in the depth direction), and the sample number increase magnification in the image enlargement part 13a of the resolution enhancement processing part 13 has been set to (Rx, Ry)=(2, 2) (where Rx is a sample number increase magnification in the scanning direction and Ry is sample number increase magnification in the depth direction).

In step S2, the transmission/reception control part 16 calculates the image size (that is, sample number) needed for the first ultrasound image D2 in order to achieve the pixel size of the second ultrasound image D3 that is the pixel size of the display image D4 or more. Here, as the pixel size needed for the first ultrasound image D2, calculation is performed such that: (x, y)=(X/Rx=250, Y/Ry=300) (where x is the sample number in the scanning direction, and y is the sample number in the depth direction).

In step S3, the transmission/reception control part 16 selects, as a transmission/reception condition to be applied, a transmission/reception condition candidate that exceeds the required sample number (x, y) and that maximizes the frame rate, out of the transmission/reception condition candidates (data table DD related to transmission/reception condition candidates in FIG. 8) preliminarily stored in the ROM 102 or the like of the apparatus main body 10. Note that it is assumed that, as the ultrasound transmission/reception conditions, the apparatus main body 10 preliminarily stores four types of transmission and reception conditions of 128, 256, 512, and 768 as the sample number (x') in the scanning direction, and preliminarily stores four types of transmission and reception conditions of 128, 256, 512, 768 as the sample number (y') in the depth direction.

In this case, from the data table DD related to the transmission/reception conditions candidate, the transmission/reception control part 16 selects the transmission/reception condition of (x', y')=(256, 512) (where x' is the sample number in the scanning direction and y is the sample number in the depth direction) so as to exceed the necessary sample number (x, y)=(X/Rx=250, Y/Ry=300) calculated in step S2 and so as to maximize the frame rate. Note that the transmission/reception condition is a condition that ultrasound transmission/reception is to be executed 256 times when the first ultrasound image D2 of one frame is generated, that is, for example, a condition of scanning within the subject such that the groups including 50 ultrasound transducers 21 as driving targets out of the 818 ultrasound transducers 21 can be shifted three at a time in the azimuth direction. Moreover, the transmission/reception condition is a condition of executing ultrasound transmission/reception at a sampling frequency that would achieve the sampling number of 512 within one scan line.

In step S4, the transmission/reception control part 16 controls the transmission/reception part 11 under the transmission/reception condition set in step S3. With this control, the image generation part 12 generates the first ultrasound image D2 of the image size set in step S3. Here, for example, the first ultrasound image D2 having an image size of (x', y')=(256, 512) is generated.

In step S5, the resolution enhancement processing part 13 applies the image enlargement processing and the forward propagation processing by CNN onto the first ultrasound image D2 generated by the image generation part 12 as described with reference to FIG. 6 and thereby generates the second ultrasound image D3. Note that here, for example, the second ultrasound image D3 having the image size of (X', Y')=(x'×Rx=512, y'×Ry=1024) (where X' is the number of pixels in the scanning direction, and Y' is the number of pixels in the depth direction) is to be generated.

In step S6, the digital scan converter 14 generates the display image D4 from the second ultrasound image D3 generated by the resolution enhancement processing part 13. Note that here the digital scan converter 14 performs size conversion, coordinate conversion, image clipping from the second ultrasound image D3 of the image size of (X', Y')=(x'×Rx=512, y'×Ry=1024) and thereby generates the display image D4 of (X, Y)=(500, 600). After step S6, the processing returns to step S4 to repeat execution of the processing of generating the first ultrasound image D2, the second ultrasound image D3, and the display image D4.

The ultrasound diagnosis apparatus 1 according to the present embodiment generates the high resolution display image D4 without reducing the frame rate by the series of processing as described above.

[Configuration of Learning Processing Part]

For example, the learning processing part 18 generates learning data from the first ultrasound image D2 generated by the image generation part 12 and applies learning processing on the CNN model Dm by using the learning data.

The learning data is, for example, a data set in which the original image of the first ultrasound image D2 generated by the image generation part 12 is defined as a correct value on the output side (corresponding to the output image D3 in FIG. 6) and the first ultrasound image D2 first reduced by the Bilinear method in accordance with the reciprocal of the sample number increase magnification and then enlarged to be a blurred image is defined as an input value (corresponding to the input image D2a in FIG. 6).

The first ultrasound image D2 to be used as learning data desirably has a high resolution as much as possible. For example, an image captured under a condition to achieve the image size being the image size of the display image D4 or more is to be used as the first ultrasound image D2. This enables the original image of the first ultrasound image D2 to be used as it is as a correct value to be set in the CNN model Dm.

Furthermore, the first ultrasound image D2 used as learning data would desirably an image set by an operator to be stored. For example, learning data is generated on the basis of the first ultrasound image D2 generated at the timing when the operator performs operation to store the display image D4. This makes it possible to set a relatively clear ultrasound image as the learning data, leading to improvement of the identification accuracy of the learned CNN model Dm.

Figure 9:
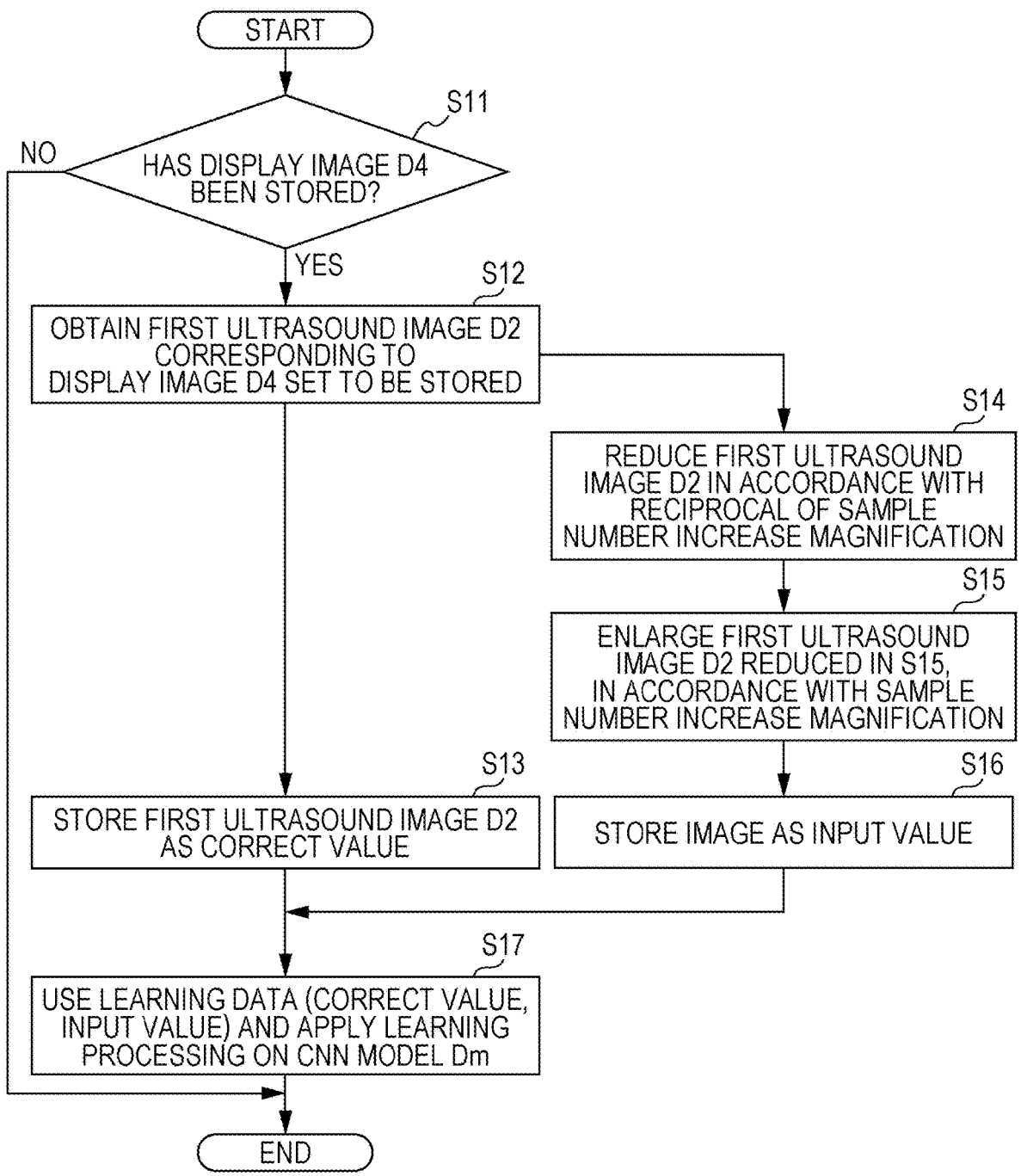
FIG. 9 is a flowchart illustrating an example of operation of the learning processing part according to the first embodiment.

FIG. 9 is a flowchart illustrating an example of operation of the learning processing part 18. Note that the flowchart of FIG. 9 is processing continuously executed by the image generation part 12 when the first ultrasound image D2 is generated.

In step S11, the learning processing part 18 determines whether the operator has performed operation of storing the display image D4. In a case where the operation of storing the display image D4 is performed in step S11 (S11: YES), the processing proceeds to step S12. In contrast, in a case where the operation of storing the display image D4 has not been performed in this step S11 (S11: NO), a series of flows is finished without executing any processing in particular.

Next, in step S12, the learning processing part 18 obtains, from the image generation part 12, the first ultrasound image D2 corresponding to the display image D4 set to be stored. Next, in step S13, the learning processing part 18 stores the original image of the first ultrasound image D2 as the correct value of the learning data.

Next, in step S14, the learning processing part 18 uses, in parallel with step S13, the Bilinear method and reduces the first ultrasound image D2 obtained in step S12 in accordance with the reciprocal of the sample number increase magnification. In step S15, the learning processing part 18 uses the Bilinear method and enlarges the first ultrasound image D2 reduced in step S14 in accordance with the sample number increase magnification. In step S16, the learning processing part 18 stores the blurred image of the first ultrasound image D2 having the same image size as the original image generated in steps S14 and S15, as an input value of the learning data.

Next, in step S17, the learning processing part 18 uses the learning data (correct value and input value) generated in steps S12 to S16 and applies learning processing on the CNN model Dm. Note that in step S17, the learning processing part 18 uses a square error as a loss function, and uses a known error back propagation method or the like and optimizes the network parameters of the CNN model Dm (weighting factor, bias, etc.) so as to minimize the loss function. Since such learning processing is similar to known processing, detailed description will be omitted here.

The series of processing as described above is used to optimize the network parameters of the CNN model Dm.

Note that, the above flowchart illustrates a mode in which the learning processing is applied on the CNN model Dm every time the learning data is generated. Note that the timing of executing the processing of the learning processing part 18 is preferably set to a non-scanning state. This makes it possible to prevent conflict between the processing of the learning processing part 18 and the processing of the resolution enhancement processing part 13.

[Effects]

As described above, in the ultrasound diagnosis apparatus 1 according to the present embodiment, the transmission/reception part 11 sequentially supplies a drive signal to each of the plurality of ultrasound transducers 21 provided in the ultrasound probe 20 such that the transmission/reception part 11 scans within the subject. At the same time, the transmission/reception part 11 receives and processes the reception signal D1 output from each of the plurality of ultrasound transducers 21. Subsequently, the image generation part 12 converts sampling data of each of positions in a cross section of the subject generated on the basis of the reception signal D1 into pixel values and generates the first ultrasound image D2. Next, the resolution enhancement processing part 13 upscales the image size of the first ultrasound image D2 in accordance with the predetermined sample number increase magnification. At the same time, the resolution enhancement processing part 13 applies image processing using the learned convolution neural network Dm on the upscaled first ultrasound image D2 and generates the second ultrasound image D3 having resolution enhanced from the first ultrasound image D2. Subsequently, the digital scan converter 14 converts the second ultrasound image D3 into the display image D4 to be displayed on the display part 15. Next, the transmission/reception control part 16 controls the transmission/reception conditions of the transmission/reception part 11 such that the image size of the second ultrasound image D3 becomes close to the image size of the display image D4 on the basis of the image size of the display image D4 and the sample number increase magnification.

Therefore, with the ultrasound diagnosis apparatus 1 according to the present embodiment, it is possible to generate the high resolution display image D4 while generating the first ultrasound image D2 under the condition that the reduced density (the number) of scan lines or the like for generating one frame. This makes it possible to display a high resolution ultrasound image on the display part 15 while generating an ultrasound image at a high frame rate.

In particular, the ultrasound diagnosis apparatus 1 according to the present embodiment is useful in that even in a case where there is an alteration in the settings of the mode setting part 17 (for example, the type of the ultrasound probe 20, the setting of the depth of the imaging target within the subject, the operation mode, or, the image size of the display image D4), it is still possible to achieve a higher frame rate and higher resolution of the display image D4 while adapting the transmission/reception conditions of the transmission/reception part 11 to the altered setting.

Second Embodiment

Next, an ultrasound diagnosis apparatus 1 according to the second embodiment will be described with reference to FIGS. 10 to 12. The ultrasound diagnosis apparatus 1 according to the present embodiment is different from the first embodiment in the configuration of the resolution enhancement processing part 13. The description of the configuration similar to the first embodiment will be omitted.

Figure 10:
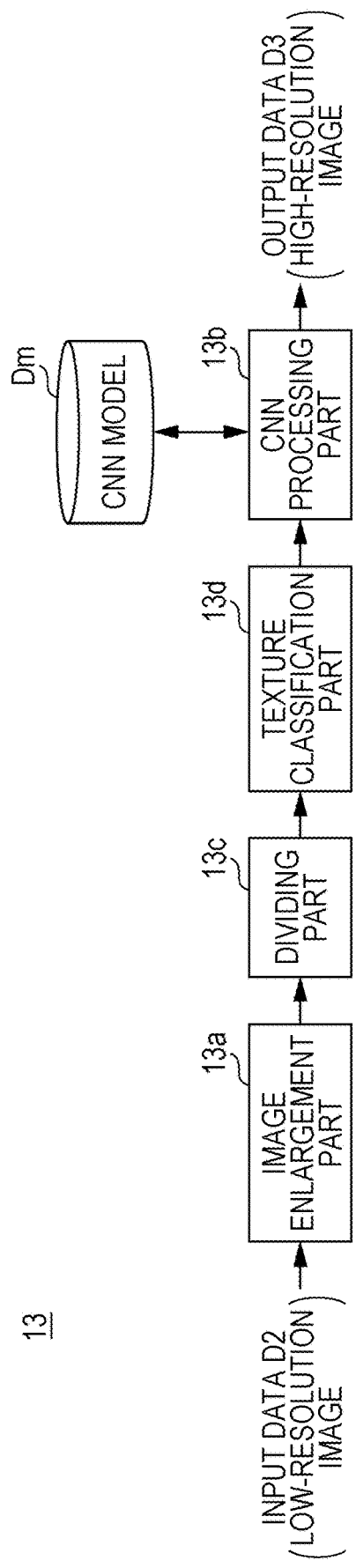
FIG. 10 is a diagram illustrating an example of a configuration of a resolution enhancement processing part according to a second embodiment.

FIG. 10 is a diagram illustrating an example of the configuration of the resolution enhancement processing part 13 according to the present embodiment. FIG. 11 is a view illustrating processing of a dividing part 13c according to the present embodiment.

The resolution enhancement processing part 13 according to the present embodiment includes the image enlargement part 13a, a dividing part 13c, a texture classification part 13d, and the CNN processing part 13b. Arrows in FIG. 10 indicate the flow of data.

The image enlargement part 13a uses general-purpose interpolation processing (for example, the Bicubic method or the Bilinear method) and enlarges the image size of the first ultrasound image in accordance with the set sample number increase magnification. The technique of enlarging the image size by the image enlargement part 13a is similar to that of the image enlargement part according to the first embodiment.

Figure 11:
FIG. 11 is a view illustrating processing of a dividing part according to the second embodiment.

The dividing part 13c divides the first ultrasound image D2a upscaled by the image enlargement part 13a into a plurality of (here, 36) small image regions R1 to R36 (refer to FIG. 11). The image sizes of the small image regions R1 to R36 set by the dividing part 13c are not particularly limited in the present invention. Still, in order to obtain a size suitable for processing by the CNN processing part 13b, the image is set to a pixel region of 11×11 pixels.

The texture classification part 13d applies texture classification processing on each of the plurality of small image regions R1 to R36 divided by the dividing part 13c. The texture classification part 13d applies known gradient estimation processing, edge detection processing, or the like, to each of the plurality of small image regions R1 to R36, for example, and thereby extracts texture (for example, luminance information and gradient information) of each of the plurality of small image regions R1 to R36. In addition, the texture classification part 13d assigns a texture classification code to each of the plurality of small image regions R1 to R36 in accordance with the texture of the small image region. The texture to be classified is preliminarily stored in the ROM 102 or the like, for example.

The technique of classifying the texture of the small image region by the texture classification part 13d may use a rule based technique, or a technique using principal component analysis, discriminant analyzer, support vector machine, neural network, or a classifier, or the like using general Hessian matrix.

In this manner, in the resolution enhancement processing part 13 according to the present embodiment uses the texture classification part 13d and preliminarily classifies the image regions (small image regions R1 to R36 divided by the dividing part 13c) to be processed by the CNN model Dm in accordance with the texture of the image region. Additionally, the resolution enhancement processing part 13 according to the present embodiment uses the CNN processing part 13b in the latter stage and applies image analysis processing using the different CNN model Dm for each of textures of the image regions. This makes it possible to reduce the size of each CNN model Dm (for example, to reduce the number of filter layers), leading to an increase in the CNN processing speed.

In order to achieve such a configuration, a plurality of CNN models Dm according to the present embodiment is provided in association with the texture classification code. In other words, the ultrasound diagnosis apparatus 1 according to the present embodiment includes a separate CNN model Dm for each of texture classification codes.

The CNN processing part 13b executes processing using CNN for each of the small image regions R1 to R36 divided by the dividing part 13c. However, the CNN processing part 13b according to the present embodiment executes image processing on the small image regions R1 to R36 using the corresponding CNN model Dm on the basis of the texture classification codes attached to the small image regions R1 to R36. Note that the image processing itself using the CNN model Dm executed by the CNN processing part 13b is similar to the case of the first embodiment.

Subsequently, the CNN processing part 13b maps an image having resolution enhanced from each of the plurality of small image regions R1 to R36 to a position corresponding to each of the plurality of small image regions R1 to R36. This leads to generation of the second ultrasound image D3.

Since the technique of resolution enhancement processing according to texture classification is similar to known methods, the detailed explanation will be omitted here (for example, Yaniv Romano, et al. "RAISR: Rapid and Accurate Image Super Resolution", arXiv: 1606.01299v3 [cs.CV], 4 Oct. 2016.

Figure 12:
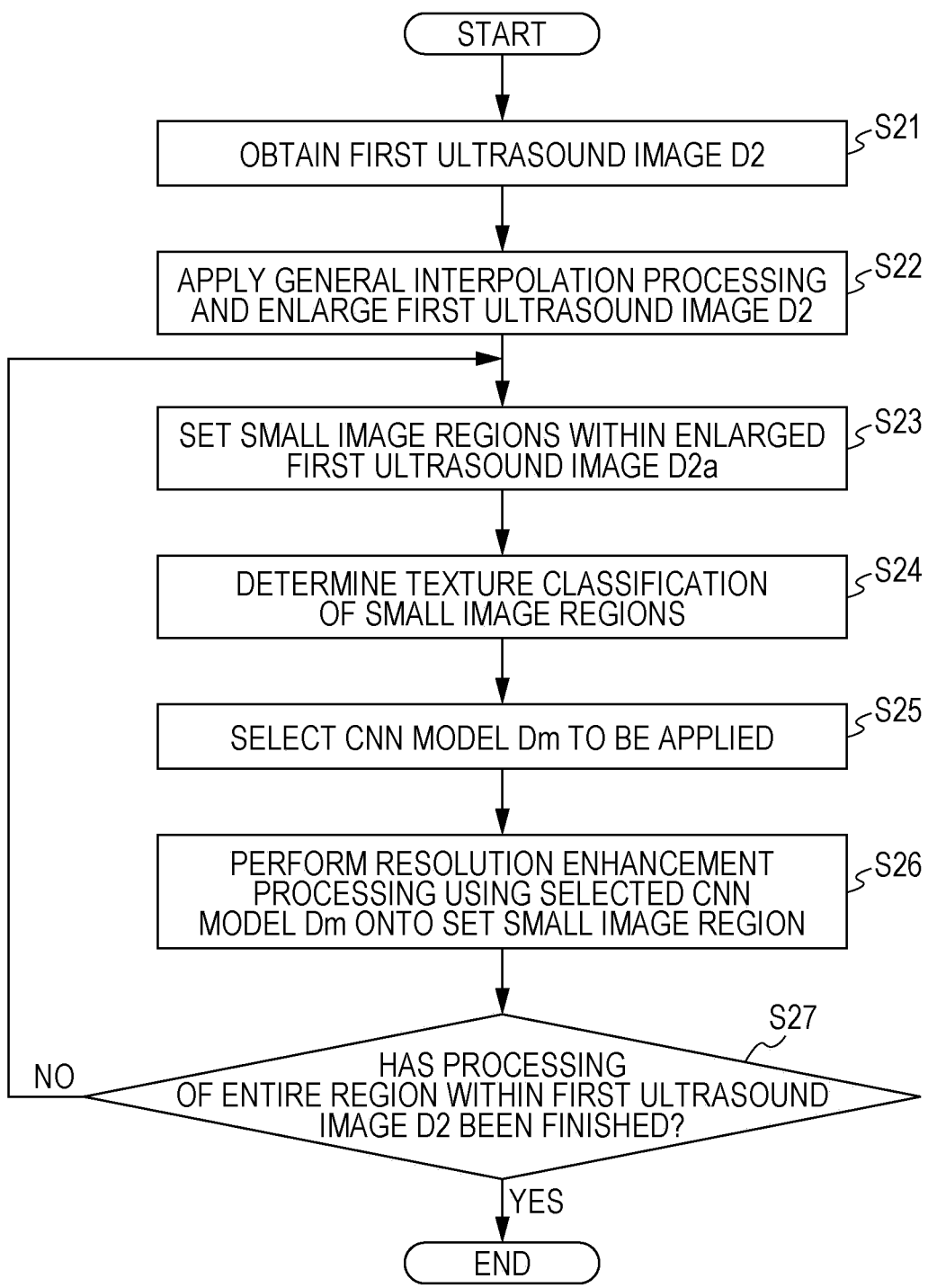
FIG. 12 is a flowchart illustrating an example of processing of the resolution enhancement processing part according to the second embodiment.

FIG. 12 is a flowchart illustrating an example of processing of the resolution enhancement processing part 13 according to the present embodiment. The flowchart of FIG. 12 includes processing executed by the resolution enhancement processing part 13 in accordance with computer programs at a predetermined interval (for example, interval of the frame rate at which the first ultrasound image D2 is generated) during the period in which the image generation part 12 generates the first ultrasound image D2.

In step S21, the resolution enhancement processing part 13 obtains the first ultrasound image D2.

In step S22, the resolution enhancement processing part 13 (the image enlargement part 13a) applies general interpolation processing and upscales the first ultrasound image D2.

In step S23, as described with reference to FIG. 11, the resolution enhancement processing part 13 (dividing part 13c) sets small image regions R1 to R36 for enlarged first ultrasound image D2 so that the enlarged first ultrasound image D2 is to be divided into the plurality of small image regions R1 to R36.

In step S24, the resolution enhancement processing part 13 (texture classification part 13d) determines the texture classification of the small image region set in step S23. At this time, the resolution enhancement processing part 13 (texture classification part 13d) applies known gradient estimation processing, edge detection processing, etc. to the small image region and extracts the texture of the small image region. The resolution enhancement processing part 13 assigns a texture classification code to the small image region corresponding to the texture of the small image region.

In step S25, the resolution enhancement processing part 13 (CNN processing part 13b) selects the CNN model Dm to be applied to the image of the small image region set in step S23, out of the plurality of CNN models Dm stored in association with the texture classification code.

In step S26, the resolution enhancement processing part 13 (CNN processing part 13b) performs resolution enhancement processing using the CNN model Dm selected in step S25, on the image of the small image region set in step S23.

In step S27, the resolution enhancement processing part 13 (dividing part 13c) determines whether processing of the entire region of the upscaled first ultrasound image D2a has been finished. In a case where the processing of the entire region has been finished (S27: YES), the resolution enhancement processing part 13 (dividing part 13c) proceeds the processing to the following step S28. In contrast, in a case where the processing of the entire region has not been finished (S27: NO), the resolution enhancement processing part 13 (dividing part 13c) returns to step S23, and shifts from the currently set small image region within the enlarged first ultrasound image, and sets the image region of the subsequent small image region as a processing target.

By repetitively executing steps S23 to S27 in this manner, the resolution enhancement processing part 13 sequentially sets the small image regions being processing targets so as to perform raster scanning of the entire region of the enlarged first ultrasound image D2. Subsequently, the resolution enhancement processing part 13 maps an image having resolution enhanced from each of the plurality of small image regions R1 to R36 to a position corresponding to each of the plurality of small image regions R1 to R36. This leads to generation of the second ultrasound image D3.

Figure 13:
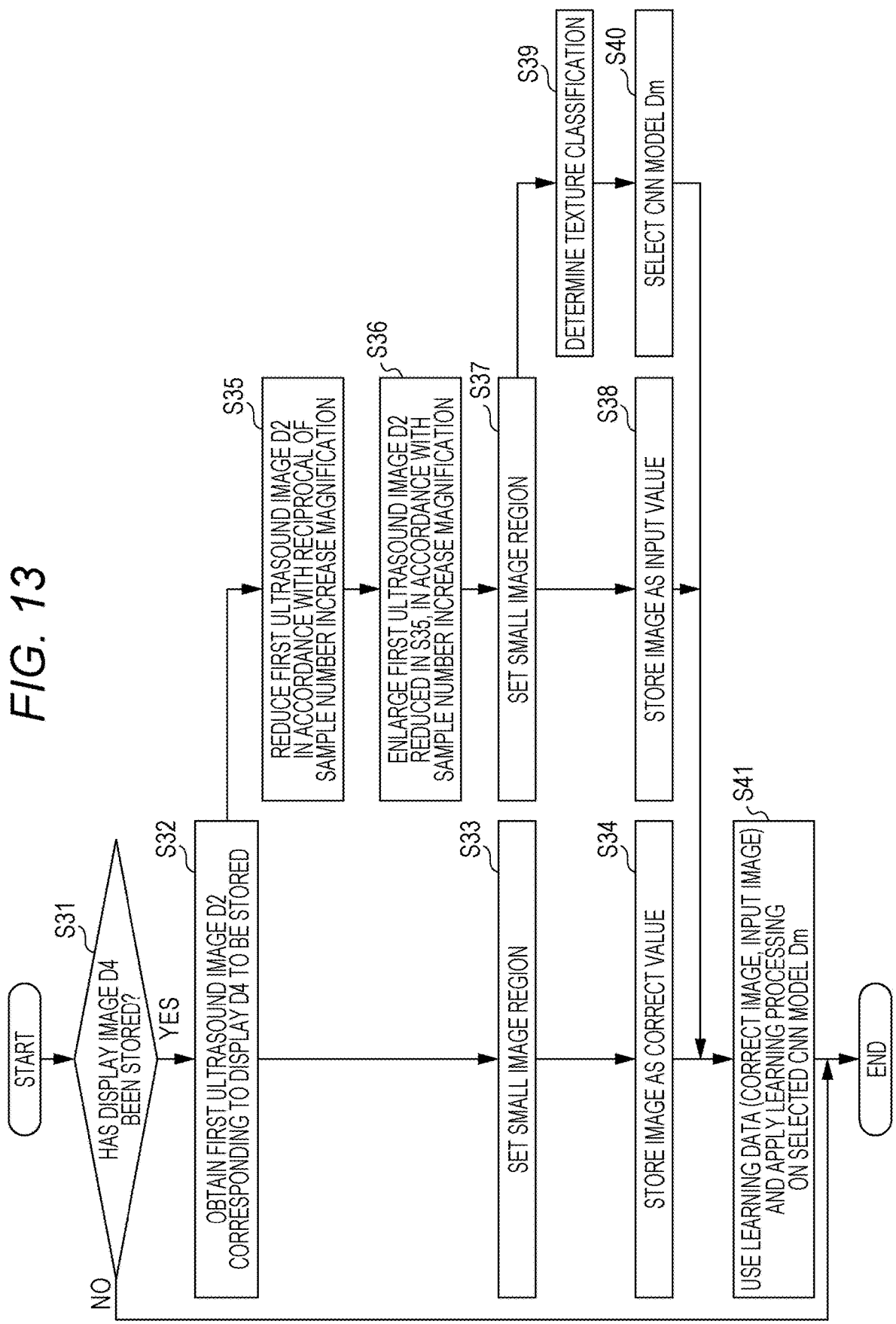
FIG. 13 is a flowchart illustrating an example of processing of a learning processing part according to the second embodiment.

FIG. 13 is a flowchart illustrating an example of processing of the learning processing part 18 according to the present embodiment. Note that the flowchart of FIG. 13 is processing continuously executed by the image generation part 12 when the first ultrasound image D2 is generated.

In the flowchart of FIG. 13, the processing (S31, S32, S35, and S36) for generating learning data is similar to the processing (S11, S12, S14, and S15) described in the flowchart of FIG. 9.

However, a plurality of pieces of data Dm of the CNN model according to the present embodiment is provided in association with the texture classification code. Accordingly, the learning processing part 18 according to the present embodiment executes learning processing for each of the pieces of data Dm of the plurality of CNN models.

In step S31, the learning processing part 18 determines whether the operator has performed the operation of storing the display image D4. In a case where it is determined in step S31 that the operation of storing the display image D4 is performed (S31: YES), the processing proceeds to step S32. In contrast, in a case where the operation of storing the display image D4 has not been performed in this step S11 (S31: NO), a series of flows is finished without executing any processing in particular.

In step S32, the learning processing part 18 obtains, from the image generation part 12, the first ultrasound image D2 corresponding to the display image D4 set to be stored.

In step S33, the learning processing part 18 sets small image regions R1 to R36 in the original image of the first ultrasound image D2. That is, the learning processing part 18 divides the original image of the first ultrasound image D2 into a plurality of small image regions R1 to R36 similarly to the dividing part 13*c* described above. In step S34, the learning processing part 18 stores the original image of the first ultrasound image D2 as a correct value of the learning data in association with the small image regions R1 to R36 set in step S33.

In step S35, in parallel to step S33, the learning processing part 18 uses the Bilinear method and reduces the first ultrasound image D2 obtained in step S32 in accordance with the reciprocal of the sample number increase magnification. Subsequently in step S36, the learning processing part 18 uses the Bilinear method and enlarges the first ultrasound image D2 reduced in step S35 in accordance with the sample number increase magnification, thereby generating a blurred image of the first ultrasound image D2.

In step S37, similarly to step S33, the learning processing part 18 sets a small image region in the blurred image of the first ultrasound image D2. In step S38, the learning processing part 18 stores the blurred image of the first ultrasound image D2 in association with the small image region set in step S37, as an input value of the learning data.

In step S39, the learning processing part 18 applies texture classification processing on each of the images of the small image region set in step S37, and assigns a texture classification code to the image of the small image region. Note that the texture classification processing is processing similar to the processing of the texture classification part 13*d* of the resolution enhancement processing part 13. In step S40, the learning processing part 18 selects the CNN model Dm to be learned out of the plurality of CNN models Dm, on the basis of the texture classification code assigned in step S39.

In step S41, the learning processing part 18 uses the learning data (correct value and input value) generated in steps S34 and S38 and applies learning processing on the CNN model Dm selected in step S40. Note that in step S41, the learning processing part 18 uses a square error as a loss function, and uses a known error back propagation method or the like and optimizes the network parameters of the CNN model Dm (weighting factor, bias, etc.) so as to minimize the loss function.

The series of processing as described above is used to optimize the individual network parameters of the CNN model Dm.

As described above, according to the ultrasound diagnosis apparatus 1 of the present embodiment, the CNN model Dm that has been learned for each of textures is prepared, and in generating the second ultrasound image D3, the convolution processing is executed by using the CNN model Dm corresponding to the CNN model Dm. Accordingly, it is possible to implement super-resolution processing with higher accuracy in a shorter time.

Third Embodiment

Next, an ultrasound diagnosis apparatus 1 according to a third embodiment will be described with reference to FIGS. 14 and 15. The ultrasound diagnosis apparatus 1 according to the present embodiment is different from the second embodiment in the configuration of the resolution enhancement processing part 13.

Figure 14:
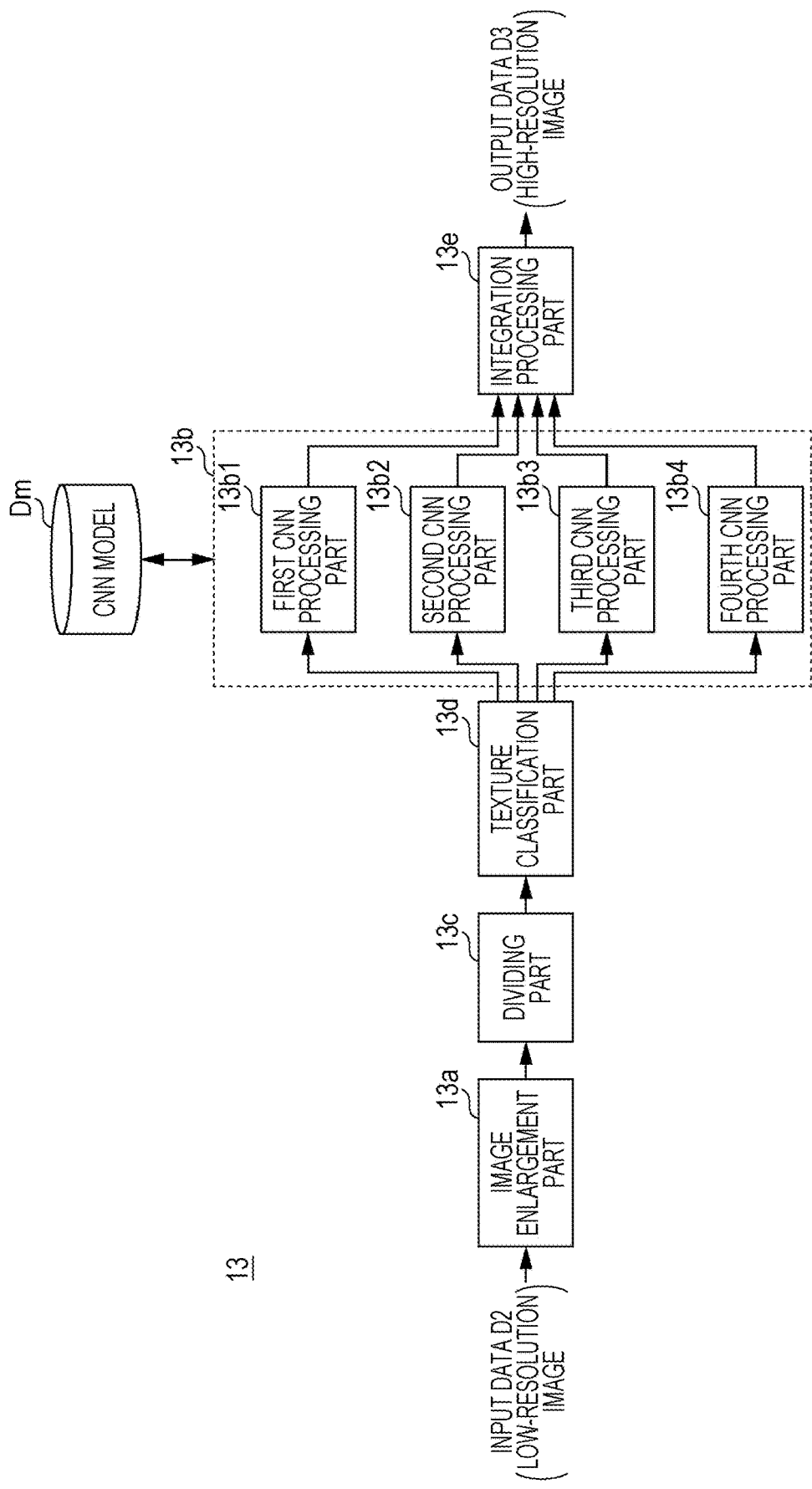
FIG. 14 is a diagram illustrating an example of a configuration of a resolution enhancement processing part according to a third embodiment.

FIG. 14 is a diagram illustrating an example of the configuration of the resolution enhancement processing part 13 according to the present embodiment. FIG. 15 is a view illustrating processing of the image enlargement part 13*a* according to the present embodiment.

The resolution enhancement processing part 13 according to the present embodiment includes the image enlargement part 13*a*, the dividing part 13*c*, the texture classification part 13*d*, the CNN processing part 13*b*, and an integration processing part 13*e*. Arrows in FIG. 14 indicate the flow of data.

The technique of enlarging the image size by the image enlargement part 13*a* is similar to that of the image enlargement part according to the first embodiment.

Figure 15:
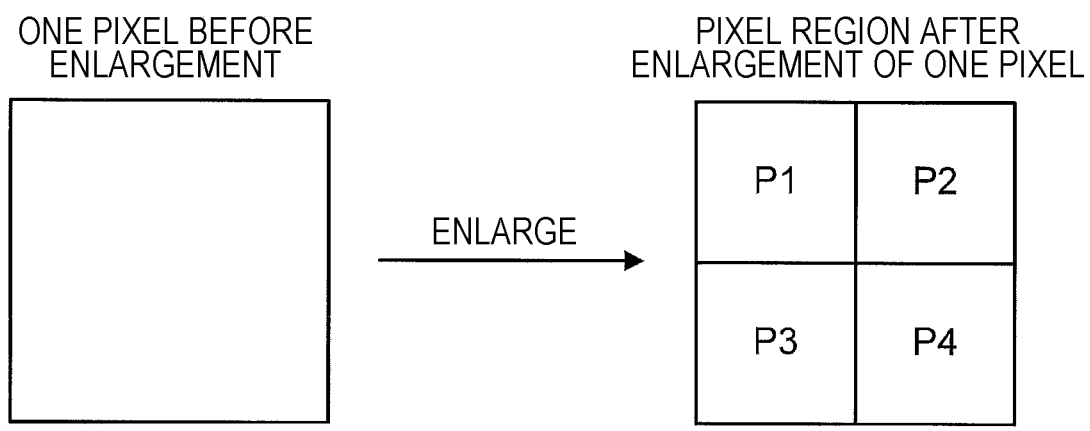
FIG. 15 is a view illustrating processing of an image enlargement part according to the third embodiment.

When the image size of the first ultrasound image D2 is enlarged, the image enlargement part 13*a* according to the present embodiment assigns a position identification code corresponding to the position of generation to each of the pixels generated by enlargement (refer to FIG. 15). FIG. 15 illustrates a position identification code to be assigned to each of pixels when the image enlargement part 13*a* enlarges the image size of the first ultrasound image D2 by 2×2. For example, the image enlargement part 13*a* assigns a position identification code of P1 to an upper left pixel, assigns a position identification code P2 to a lower left pixel, assigns a position identification code P3 to a lower left pixel, and assigns a position identification code of P4 to a lower right pixel, among the pixel regions of four pixels generated as a result of enlarging one pixel before enlargement by 2×2 times. While FIG. 15 illustrates one pixel alone, the image enlargement part 13*a* assigns the position identification codes P1 to P4 to all the pixels in accordance with a similar rule. That is, for each of the plurality of pixels generated by upscaling the first ultrasound image D2, an identification code is set on the basis of the positional relationship with the pixel referred to when the first ultrasound image D2 is generated.

The configuration of the dividing part 13*c* and the texture classification part 13*d* is similar to that of the second embodiment.

In order to achieve such a configuration, the CNN model Dm according to the present embodiment is provided in plurality in association with the position identification codes P1 to P4 and the texture classification code. In other words, the ultrasound diagnosis apparatus 1 according to the present embodiment includes different CNN model data Dm for each of position identification code and texture classification codes.

That is, the data Dm of the CNN model includes: a first CNN model Dm that selectively processes an image to which the position identification code P1 is assigned as a processing target; a second CNN model Dm that selectively processes an image to which the position identification code P2 is assigned as a processing target; a third CNN model Dm that selectively processes an image to which the position identification code P3 is assigned as a processing target; and a fourth CNN model Dm that selectively processes an image to which the position identification code P4 is assigned as a processing target. Additionally, each of the first to fourth CNN models Dm has a different CNN model Dm for each of the texture classification codes.

The CNN processing part 13b includes a first CNN processing part 13b1, a second CNN processing part 13b2, a third CNN processing part 13b3, and a fourth CNN processing part 13b4.

Here, the first CNN processing part 13b1 executes resolution enhancement processing using the CNN model Dm with which the position identification code P1 is associated onto the image to which the position identification code P1 is assigned, and thereby generates a first resolution enhanced image. In addition, the second CNN processing part 13b2 executes resolution enhancement processing using the CNN model Dm with which the position identification code P2 is associated onto the image to which the position identification code P2 is assigned, and thereby generates a second resolution enhanced image. In addition, the third CNN processing part 13b3 executes resolution enhancement processing using the CNN model Dm on the image to which the position identification code P3 is assigned, and thereby generates a third resolution enhanced image. In addition, the fourth CNN processing part 13b4 executes resolution enhancement processing using the CNN model Dm with which the position identification code P4 is associated on the image to which the position identification code P4 is assigned, and thereby generates a fourth resolution enhanced image.

In other words, the CNN processing part 13b according to the present embodiment divides the image into four images, namely, an image at a position to which the position identification code P1 is assigned, an image at a position to which the position identification code P2 is assigned, an image at the position to which the position identification code P3 is assigned, and an image at a position to which the position identification code P4 is assigned. The divided four images are respectively input to the first CNN processing part 13b1, the second CNN processing part 13b2, the third CNN processing part 13b3, and the fourth CNN processing part 13b4.

The first CNN processing part 13b1 executes processing using the CNN model Dm for the image at the position to which the position identification code P1 is assigned, for each of the small image regions R1 to R36. The second CNN processing part 13b2 executes processing using the CNN model Dm for the image at the position to which the position identification code P2 is assigned, for each of the small image regions R1 to R36. The third CNN processing part 13b3 executes processing using the CNN model Dm for the image at the position to which the position identification code P3 is assigned, for each of the small image regions R1 to R36. The fourth CNN processing part 13b4 executes processing using the CNN model Dm for the image at the position to which the position identification code P4 is assigned, for each of the small image regions R1 to R36.

The image processing itself using the CNN model Dm executed in each of the first CNN processing part 13b1, the second CNN processing part 13b2, the third CNN processing part 13b3, and the fourth CNN processing part 13b4 is similar to the case of the first embodiment.

The integration processing part 13e integrates the first to fourth resolution enhanced images generated by the CNN processing part 13b. Here, each of the first to fourth resolution enhanced images is an image having the same image size as the input image. For example, the integration processing part 13e maps the first resolution enhanced image corresponding to the position of the pixel to which the position identification code P1 is assigned, maps the second resolution enhanced image corresponding to the position of the pixel to which the position identification code P2 is assigned, maps the third resolution enhanced image corresponding to the position of the pixel to which the position identification code P3 is assigned, and maps the fourth resolution enhanced image corresponding to the position of the pixel to which the position identification code P4 is assigned. This integrates the first to fourth resolution enhanced images, generating the second ultrasound image D3.

Since the technique of resolution enhancement processing is similar to known methods, the detailed explanation will be omitted here (for example, Yaniv Romano, et al. "RAISR: Rapid and Accurate Image Super Resolution", arXiv: 1606.01299v3 [cs.CV], 4 Oct. 2016.

As described above, according to the resolution enhancement processing part 13 of the present embodiment, image processing using different CNN models Dm is executed for each of positions of pixels generated by upscaling the first ultrasound image D2. Accordingly, it is possible to implement super-resolution processing with higher accuracy.

Other Embodiments

The present invention is not limited to the above embodiment, and various modifications are conceivable.

As an example of the resolution enhancement processing part 13, the above embodiment presents a mode in which an identical CNN model Dm is applied to the different type or different imaging modes of the ultrasound probe 20. However, the texture of the first ultrasound image D2 varies greatly depending on the type of the ultrasound probe 20 or the imaging mode (B-mode, C-mode, or E-mode, for example). From such a viewpoint, the resolution enhancement processing part 13 may use different CNN models Dm depending on the type or the imaging mode of the ultrasound probe 20.

Moreover, as an example of the transmission/reception control part 16, the above embodiment has presented a mode of simultaneously executing transmission and reception of ultrasound in groups of 50 ultrasound transducers 21 adjacent to each other. However, the mode in which the transmission/reception control part 16 drives the ultrasound transducers 21 can be set to any modes. For example, the ultrasound beam may be formed with phases shifted in the ultrasounds simultaneously transmitted from a group of ultrasound transducers 21 to be driven. Alternatively, the ultrasound beam may be formed with the phases aligned in the ultrasounds simultaneously transmitted from the group of ultrasound transducers 21 to be driven. Moreover, the transmission/reception control part 16 may drive the plurality of ultrasound transducers 21 arranged in the azimuth direction one by one.

Furthermore, the above embodiment has described, as an example of the configuration of the ultrasound diagnosis apparatus 1, a configuration in which the image generation part 12, the resolution enhancement processing part 13, the digital scan converter 14, the transmission/reception control part 16, the mode setting part 17, and the learning processing part 18 are implemented by one computer. However, it is a matter of course that the configuration including these may be implemented by a plurality of computers.

The above embodiment has described, as an example of the operation of the ultrasound diagnosis apparatus 1, a configuration in which the image generation part 12, the resolution enhancement processing part 13, and the digital scan converter 14 are executed in a series of flows. However, it is a matter of course that that some or all of these processing may be executed in parallel.

Moreover, the above embodiment has presented a mode of generating a B-mode image, as an example of the ultrasound diagnosis apparatus 1. Alternatively, however, the ultrasound diagnosis apparatus 1 according to the present invention may generate a color Doppler image, an elastic image, a three-dimensional ultrasound image, an M-mode image, or the like. Similarly, the ultrasound probe 20 may be implemented by using any of a convex probe, a linear probe, a sector probe, a three-dimensional probe, or the like.

According to the ultrasound diagnosis apparatus of the present disclosure, it is possible to increase the resolution of the ultrasound image displayed by the display part without deteriorating the frame rate.

Although embodiments of the present invention have been described and illustrated in detail, the disclosed embodiments are made for purposes of illustration and example only and not limitation. The scope of the present invention should be interpreted by terms of the appended claims. Technologies described in the claims include specific examples above that have been modified and altered in various manners.

What is claimed is:

1. An ultrasound diagnosis apparatus comprising:
   a transmission/reception part configured to sequentially supply a drive signal to each of a plurality of ultrasound transducers provided in an ultrasound probe so as to scan within a subject, and receive and process reception signals output from each of the plurality of ultrasound transducers; and
   a hardware processor configured to:
   determine, based on a set image size of a display image and a predetermined sample number increase magnification, transmission/reception conditions of the transmission/reception part required to achieve a pixel size of a second ultrasound image that is a pixel size of the display image or more and to maximize the frame rate;
   control the transmission/reception part to use the determined transmission/reception conditions;
   convert signal strengths of the reception signals of each of positions within the subject into pixel values, and generate a first ultrasound image;
   upscale the first ultrasound image in accordance with the predetermined sample number increase magnification, and thereafter apply resolution enhancement processing on the first ultrasound image and generate the second ultrasound image; and
   convert the second ultrasound image into the display image to be displayed on a display part,
   wherein the transmission/reception conditions include a number of scan lines or density of scan lines and a sampling frequency defining frequency at which sampling is performed in one scan line, and the transmission/reception conditions are determined by selecting transmission/reception condition candidates from a predetermined group of transmission/reception condition candidates.

2. The ultrasound diagnosis apparatus according to claim 1,
   wherein the resolution enhancement processing is image processing using a learned convolution neural network.

3. The ultrasound diagnosis apparatus according to claim 2,
   wherein the convolution neural network is configured to define the first ultrasound image generated by the hardware processor as a correct value, apply reduction processing on the first ultrasound image in accordance with a reciprocal of the sample number increase magnification to obtain a reduced first ultrasound image, apply enlargement processing on the reduced first ultrasound image in accordance with the sample number increase magnification to obtain an input value, and thereafter perform learning processing using the correct value and the input value as learning data.

4. The ultrasound diagnosis apparatus according to claim 3,
   wherein the hardware processor is configured to, when an operator performs an operation to store the display image based on the first ultrasound image, store the first ultrasound image as the learning data.

5. The ultrasound diagnosis apparatus according to claim 3,
   wherein the hardware processor is configured to set the execution of the learning processing to be performed during a non-scanning state.

6. The ultrasound diagnosis apparatus according to claim 3, wherein the hardware processor includes:
   an image enlargement part that is configured to use image interpolation processing and upscale an image size of the first ultrasound image in accordance with the sample number increase magnification;
   a dividing part that is configured to divide the upscaled first ultrasound image into a plurality of image regions;
   a texture classification part that configured to extract texture of each of the plurality of image regions and classify each of the plurality of image regions on the basis of the texture of the image region; and
   a CNN processing part that is configured to use the learned convolution neural network corresponding to the texture of the image region out of the plurality of prepared learned convolution neural networks, apply image processing on each of the plurality of image regions, and generate the second ultrasound image.

7. The ultrasound diagnosis apparatus according to claim 6,
   wherein the texture of the image region used as a reference by the texture classification part includes luminance information or gradient information of the image region.

8. The ultrasound diagnosis apparatus according to claim 1,
   wherein the hardware processor is configured to set the image size of the display image on the basis of a type of the ultrasound probe, a depth of an imaging target within the subject, or an imaging mode.

9. The ultrasound diagnosis apparatus according to claim 1,
wherein the hardware processor is configured to set the sample number increase magnification based on the depth of an imaging target within the subject.

10. The ultrasound diagnosis apparatus according to claim 1,
wherein the hardware processor is configured to set the sample number increase magnification and the pixel size of the display image is set on the basis of an operator's input operation.

11. The ultrasound diagnosis apparatus according to claim 1,
wherein the sample number increase magnification is an integer of two or more.

12. The ultrasound diagnosis apparatus according to claim 1,
wherein the image size of the display image is a setting that defines the number of pixels in a scan direction and a number of pixels in a depth direction.

\* \* \* \* \*